US012690902B2

(12) United States Patent
Siddiqui et al.

(10) Patent No.: US 12,690,902 B2
(45) Date of Patent: Jul. 28, 2026

(54) INTRAMEDULLARY IMPLANT SYSTEMS AND METHODS

(71) Applicant: ARTHREX, INC., Naples, FL (US)

(72) Inventors: Noman Siddiqui, Baltimore, MD (US); Zachary Day, Naples, FL (US)

(73) Assignee: ARTHREX, INC., Naples, FL (US)

( * ) Notice: Subject to any disclaimer, the term of this patent is extended or adjusted under 35 U.S.C. 154(b) by 121 days.

(21) Appl. No.: 18/321,973

(22) Filed: May 23, 2023

(65) Prior Publication Data

US 2023/0310043 A1    Oct. 5, 2023

Related U.S. Application Data

(62) Division of application No. 17/267,531, filed as application No. PCT/US2019/046147 on Aug. 12, 2019, now abandoned.

(60) Provisional application No. 62/718,656, filed on Aug. 14, 2018.

(51) Int. Cl.
| | |
|---|---|
| *A61B 17/72* | (2006.01) |
| *A61B 17/80* | (2006.01) |
| *A61B 17/56* | (2006.01) |

(52) U.S. Cl.
CPC ........ *A61B 17/7233* (2013.01); *A61B 17/725* (2013.01); *A61B 17/7291* (2013.01); *A61B 17/8057* (2013.01); *A61B 2017/565* (2013.01)

(58) Field of Classification Search
CPC .............. A61B 17/7233; A61B 17/725; A61B 17/7291; A61B 17/8057; A61B 2017/565
See application file for complete search history.

(56) References Cited

U.S. PATENT DOCUMENTS

| | | | | |
|---|---|---|---|---|
| 4,204,531 | A | 5/1980 | Aginsky | |
| 5,057,103 | A | 10/1991 | Davis | |
| 5,893,850 | A | 4/1999 | Cachia | |
| 5,971,986 | A | 10/1999 | Santori et al. | |
| 6,248,109 | B1 * | 6/2001 | Stoffella ................ | A61B 17/68 |
| | | | | 606/62 |
| 6,348,053 | B1 | 2/2002 | Cachia | |
| 6,554,833 | B2 | 4/2003 | Levy et al. | |
| 6,575,973 | B1 * | 6/2003 | Shekalim .......... | A61B 17/7266 |
| | | | | 606/68 |
| 6,689,136 | B2 | 2/2004 | Stoffella | |
| 6,706,046 | B2 | 3/2004 | Orbay et al. | |

(Continued)

FOREIGN PATENT DOCUMENTS

| | | |
|---|---|---|
| CN | 204655083 U | 9/2015 |
| DE | 202016000715 U1 | 4/2016 |

(Continued)

OTHER PUBLICATIONS

International Search Report and Written Opinion of the International Searching Authority for International application No. PCT/US2019/046147 dated Dec. 17, 2019.

(Continued)

*Primary Examiner* — Nicholas J Plionis

(74) *Attorney, Agent, or Firm* — Carlson, Gaskey & Olds, P.C.

(57) ABSTRACT

Exemplary intramedullary implant systems are provided for performing surgical procedures. The intramedullary implant systems may be used for performing bone fracture, bone fusion, or osteotomy procedures within joints.

23 Claims, 14 Drawing Sheets

(56) References Cited

U.S. PATENT DOCUMENTS

| | | | |
|---|---|---|---|
| 6,730,090 | B2 | 5/2004 | Orbay et al. |
| 7,052,498 | B2 | 5/2006 | Levy et al. |
| 7,563,263 | B2 | 7/2009 | Orbay et al. |
| 7,601,152 | B2 | 10/2009 | Levy et al. |
| 7,670,339 | B2 | 3/2010 | Levy et al. |
| 7,727,264 | B2 | 6/2010 | Orbay et al. |
| 7,909,880 | B1 | 3/2011 | Grant |
| 7,938,850 | B2 | 5/2011 | Orbay et al. |
| 8,460,343 | B2 | 6/2013 | Graham |
| 8,491,584 | B1 | 7/2013 | Fagan |
| 8,685,024 | B2 | 4/2014 | Roman |
| 8,696,719 | B2 | 4/2014 | Lofthouse et al. |
| 8,740,915 | B2 | 6/2014 | Niederberger et al. |
| 8,828,063 | B2 | 9/2014 | Blitz et al. |
| 8,876,822 | B2 | 11/2014 | Fagan et al. |
| 8,888,778 | B2 | 11/2014 | Roman |
| 9,005,255 | B2 | 4/2015 | Lewis et al. |
| 9,060,822 | B2 | 6/2015 | Lewis et al. |
| 9,308,035 | B2 | 4/2016 | Biedermann et al. |
| 9,433,449 | B2 | 9/2016 | Vega et al. |
| 9,629,671 | B2 | 4/2017 | Roman |
| 9,668,793 | B2 | 6/2017 | Gaudin |
| 9,788,871 | B2 | 10/2017 | Simon |
| 9,788,958 | B2 | 10/2017 | Melamed et al. |
| 9,814,499 | B2 | 11/2017 | Buscaglia et al. |
| 9,867,642 | B2 | 1/2018 | Simon |
| 9,895,179 | B2 | 2/2018 | Roman |
| 2004/0153073 | A1 | 8/2004 | Orbay |
| 2005/0187555 | A1* | 8/2005 | Biedermann .......... A61B 17/74 |
| | | | 606/301 |
| 2006/0189987 | A1* | 8/2006 | Orbay ................ A61B 17/8888 |
| | | | 606/62 |
| 2007/0083202 | A1 | 4/2007 | Eli Running et al. |
| 2007/0233103 | A1* | 10/2007 | Metzinger ............ A61B 17/744 |
| | | | 606/62 |
| 2009/0036931 | A1 | 2/2009 | Pech et al. |
| 2010/0152786 | A1 | 6/2010 | Behrbalk |
| 2011/0087227 | A1 | 4/2011 | Mazur et al. |
| 2012/0209334 | A1 | 8/2012 | Lewis et al. |
| 2013/0204250 | A1* | 8/2013 | McDevitt .......... A61B 17/7233 |
| | | | 606/62 |
| 2015/0272639 | A1 | 10/2015 | Lewis et al. |
| 2015/0327900 | A1 | 11/2015 | Toro et al. |
| 2016/0074079 | A1 | 3/2016 | Leemrijse et al. |
| 2016/0081728 | A1 | 3/2016 | McCormick |
| 2016/0135858 | A1 | 5/2016 | Dacosa et al. |
| 2016/0354127 | A1 | 12/2016 | Lundquist et al. |
| 2017/0196602 | A1 | 7/2017 | Lundquist et al. |
| 2017/0238978 | A1 | 8/2017 | Lewis et al. |
| 2018/0070995 | A1* | 3/2018 | Kay ................... A61B 17/8061 |
| 2018/0092674 | A1* | 4/2018 | McDaniel .......... A61B 17/7291 |
| 2019/0125418 | A1 | 5/2019 | Muller |

FOREIGN PATENT DOCUMENTS

| | | |
|---|---|---|
| EP | 1952776 A1 | 8/2008 |
| EP | 3476319 A2 | 5/2019 |

OTHER PUBLICATIONS

Mini Maxlock Extreme ISO Plate, Surgical Technique, Wright Focused Excellence, 12 pages, MXM 801-002 Rev A ECN 160491 Apr. 13, 2016.

Mini Maxlock Extreme Small Plate and Screw System, Wright Focused Excellence, four pages, MXM 802-001 Rev A EN 160494 Apr. 13, 2016.

Virtual Patent Marking, Wright Focused Excellence, 51 pages, VPR Mar. 20, 2018 http://www.wright.com/corporate/patent-information.

International Preliminary Report on Patentability for International application No. PCT/US2019/046147 dated Feb. 25, 2021.

* cited by examiner

INTRAMEDULLARY IMPLANT SYSTEMS AND METHODS

CROSS-REFERENCE TO RELATED APPLICATION

This is a divisional of U.S. application Ser. No. 17/267,531, filed on Feb. 10, 2021, which is a national stage application of International Application No. PCT/US2019/046147, filed on Aug. 12, 2019, which claims priority to U.S. Provisional Patent Application No. 62/718,656, filed on Aug. 14, 2018, the entire disclosure of which is incorporated herein by reference.

BACKGROUND

This disclosure relates to intramedullary implant systems and associated surgical methods.

A variety of surgical implants are used to treat bone abnormalities such as fractures and bunions. For example, bone plates and intramedullary nails are commonly employed during orthopedic surgeries to stabilize, fuse, and/or align bones or bone fragments in order to restore functionality to a joint.

SUMMARY

This disclosure relates to intramedullary implant systems for performing bone fracture procedures, bone fusion procedures, osteotomy procedures, etc.

A first exemplary intramedullary implant system may include, inter alia, an implant including a plate portion and an integral intramedullary portion, a locking screw received through an opening of the plate portion, and a crossing screw received through an additional opening of the plate portion or the integral intramedullary portion. The crossing screw may extend at a non-perpendicular angle relative to a centerline axis of the implant.

Another exemplary intramedullary implant system may include an implant including a plate portion and an integral intramedullary portion. Talons (e.g., wings, barbs, claws, etc.) may be provided on the intramedullary portion. The talons may be configured to deploy from a first position to a second position to increase stability of the implant relative to a bone.

Another exemplary intramedullary implant system may include, inter alia, an implant that includes a plate portion and an integral intramedullary portion. The implant may be made of a shape memory material.

Another exemplary intramedullary implant system may include, inter alia, an intramedullary nail, a plate, a washer, and first and second fixation devices. The first fixation device may connect the plate to the intramedullary nail, and the second fixation device may connect the washer to the intramedullary nail.

DETAILED DESCRIPTION

Figure 1:
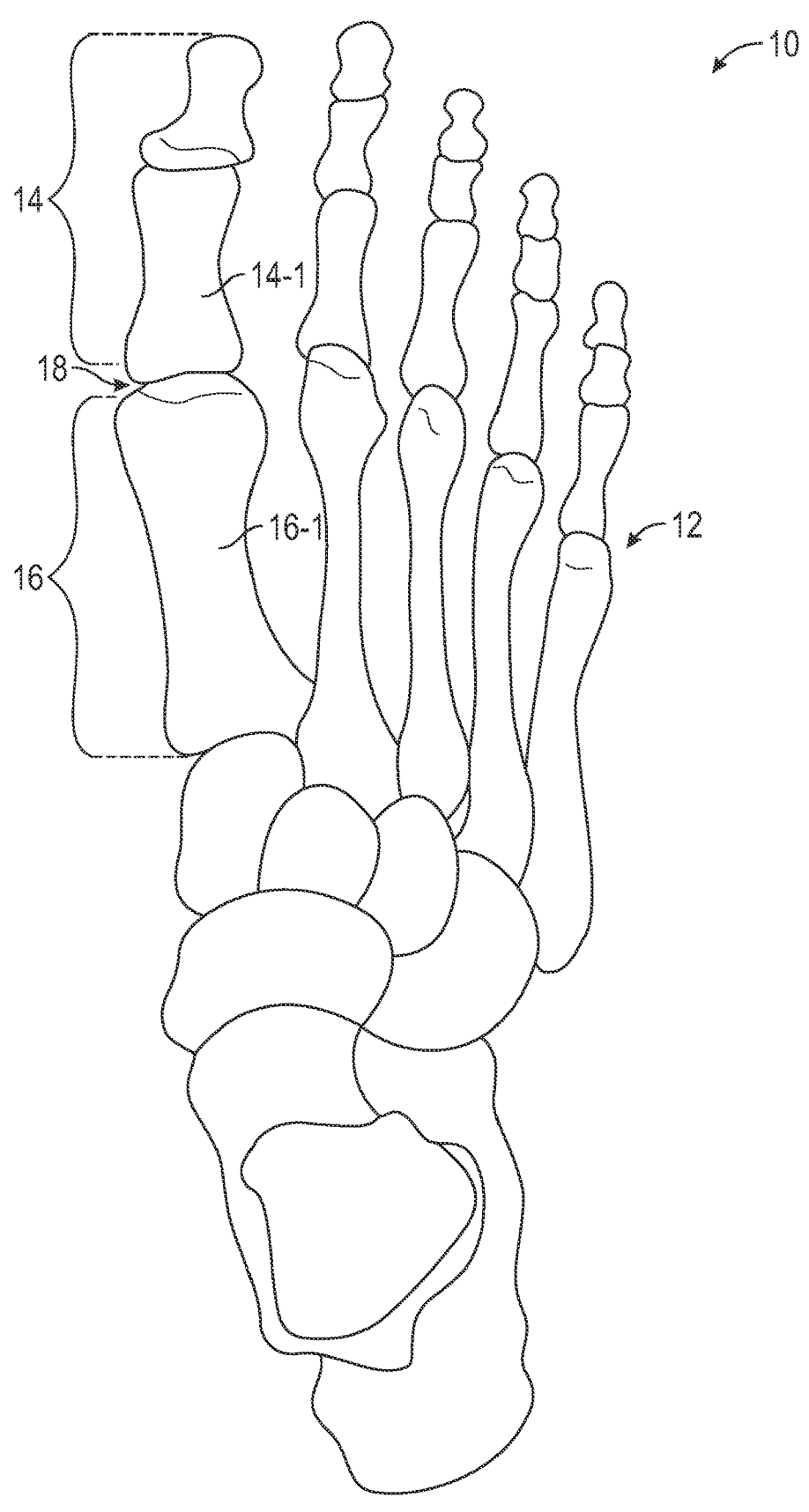
FIG. 1 illustrates a foot of the human musculoskeletal system. The foot includes a bone abnormality.

This disclosure describes exemplary intramedullary implant systems for performing bone fracture, bone fusion, or osteotomy procedures within joints.

A first exemplary intramedullary implant system may include, inter alia, an implant including a plate portion and an integral intramedullary portion, a locking screw received through an opening of the plate portion, and a crossing screw received through an additional opening of the plate portion or the integral intramedullary portion. The crossing screw may extend at a non-perpendicular angle relative to a centerline axis of the implant.

In a further embodiment, talons are provided on an integral intramedullary portion of an implant. The talons are configured to deploy from a first position to a second position to increase stability of the implant relative to a bone.

In a further embodiment, talons are provided on a proximal portion of an integral intramedullary portion of an implant.

In a further embodiment, talons of an integral intramedullary implant portion of an implant include deployable wings, barbs, claws, or any combinations thereof.

In a further embodiment, a plate portion is laterally offset from an integral intramedullary portion of an implant.

In a further embodiment, a centerline axis of an implant is non-linear.

In a further embodiment, portions of a plate portion of an implant, an integral intramedullary portion of the implant, or both are curved.

In a further embodiment, an integral intramedullary portion of an implant is configured in the shape of a nail body. An additional opening is formed through the nail body for receiving a crossing screw.

In a further embodiment, a plate portion and an integral intramedullary portion of an implant are comprised of a shape memory material.

In a further embodiment, a shape memory material of an implant includes Nitinol, and a centerline axis of the implant is curved.

In a further embodiment, a tab protrudes from an integral intramedullary portion of an implant near a junction between the integral intramedullary portion and a plate portion of the implant. An additional opening is formed through the tab for receiving a crossing screw.

Another exemplary intramedullary implant system may include, inter alia, an intramedullary nail, a plate, a washer, and first and second fixation devices. The first fixation device may connect the plate to the intramedullary nail, and the second fixation device may connect the washer to the intramedullary nail.

In a further embodiment, a third fixation device extends through an intramedullary nail but is unconnected to either a plate or a washer of an intramedullary implant system.

In a further embodiment, a plate of an intramedullary implant system includes a groove located on a bone facing surface of the plate, an opening for receiving a first fixation device, and a suture hole configured for receiving a suture, filament, or other thread-like material.

In a further embodiment, a washer of an intramedullary implant system includes a central opening for receiving the second fixation device and a plurality of suture holes surrounding the central opening and configured for receiving a suture, filament, or other thread-like material.

FIG. 1 schematically illustrates portions of a foot 10 of the human musculoskeletal system. A forefoot 12 of the foot 10 is specifically shown. The forefoot 12 includes multiples phalanges 14 (i.e., toes) and multiples metatarsals 16 located proximal to the phalanges 14. As illustrated, the foot 10 includes a bone abnormality 18. In an embodiment, the bone abnormality 18 is a hallux valgus abnormality (also referred to as a bunion abnormality) in which there is a medial deviation of the first metatarsal 16-1 and a lateral deviation of the first phalanges 14-1. If not corrected, the bone abnormality 18 can lead to pain and arthritis.

Figure 2:
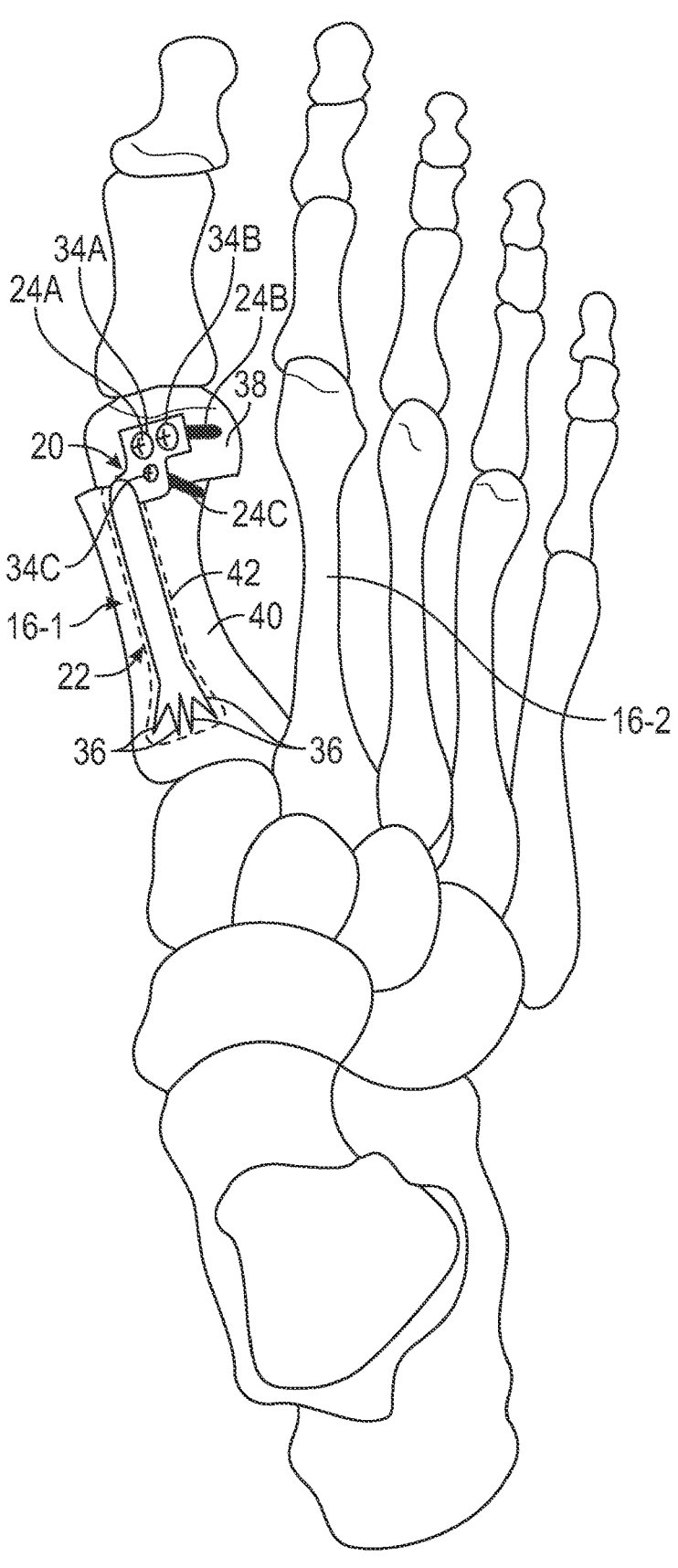
FIG. 2 illustrates an exemplary intramedullary implant system for correcting the bone abnormality of FIG. 1.
Figure 3:
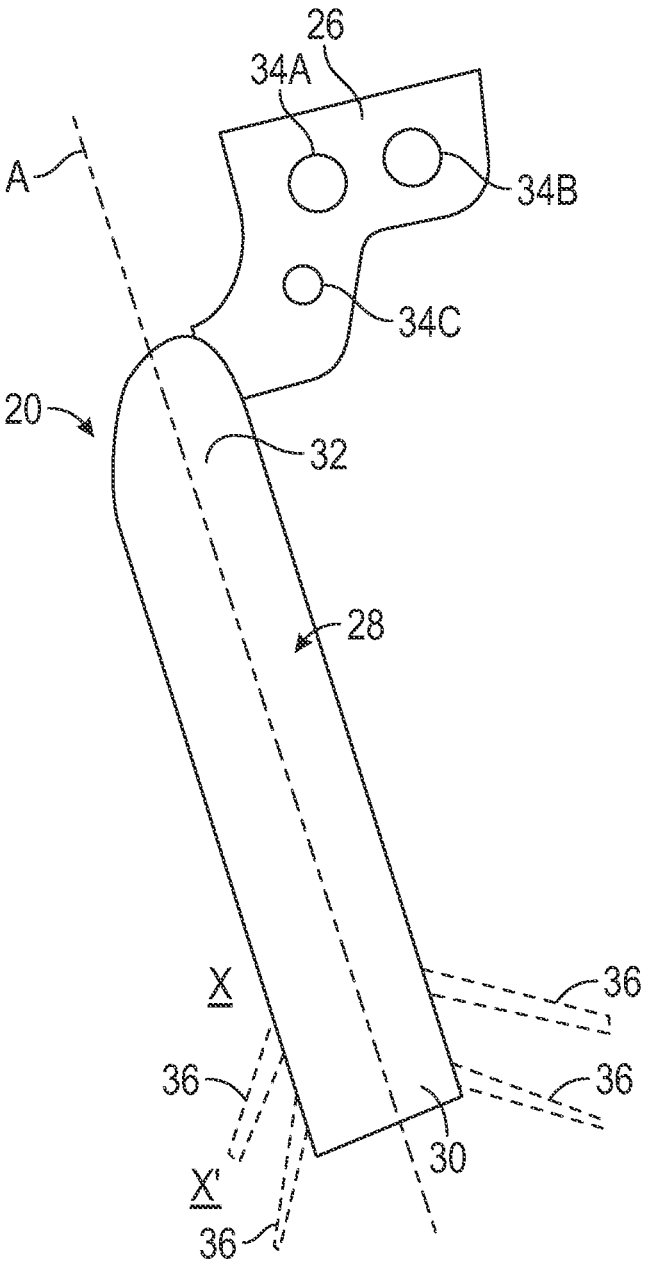
FIG. 3 further illustrates the intramedullary implant system of FIG. 2.

FIGS. 2-3 illustrate an intramedullary implant system 20 for repairing the bone abnormality 18 of FIG. 1. The intramedullary implant system 20 may include an implant 22 and a multitude of fixation devices 24 (e.g., screws, pegs, etc.). The total number of fixation devices 24 utilized within the intramedullary implant system 20 is not intended to limit this disclosure.

The implant 22 may include a plate portion 26 and an intramedullary portion 28. In an embodiment, the plate portion 26 and the intramedullary portion 28 are integrated to establish a single-piece structure. Stated another way, the implant 22 may be a monolithic device without any mechanical attachments for connecting the plate portion 26 and the intramedullary portion 28 together.

The intramedullary portion 28, which may be configured in the shape of a nail body, may extend along a longitudinal centerline axis A between a proximal portion 30 and a distal portion 32. The plate portion 26 may include any size and shape. The distal portion 32 connects to the plate portion 26 of the implant 22, whereas the proximal portion 30 is disposed at an opposite end of the intramedullary portion 28 from the plate portion 26.

In an embodiment, the plate portion 26 is offset from the intramedullary portion 28. For example, the plate portion 26 may be laterally offset from the longitudinal centerline axis A of the intramedullary portion. The offset between the plate portion 26 and the intramedullary portion 28 can be any offset distance within the scope of this disclosure (e.g., 3 mm, 5 mm, 7 mm, 10 mm, etc.).

The plate portion 26, the intramedullary portion 28, or both may include openings for receiving the fixation devices 24. In an embodiment, the plate portion 26 includes a first opening 34A for receiving a first fixation device 24A, a second opening 34B for receiving a second fixation device 24B, and a third opening 34C for receiving a third fixation device 24C. The first and second fixation devices 24A and 24B may be locking screws and the third fixation device 24C may be a crossing screw, in an embodiment.

In another embodiment, the intramedullary portion 28 of the implant 22 includes one or more deployable talons 36. The talons 36 may be configured as deployable wings, barbs, claws, etc. that extend from the implant 22 to enhance the intramedullary boney fixation. The talons 36 may also provide rotational stability once deployed. During removal, the talons 36 may be retracted to safely remove the implant 22 from the intramedullary canal.

The talons 36 may be selectively deployed between a first position X and a second positon X' (shown in phantom in FIG. 3). In the deployed positon X', the talons 36 grip surrounding bone and therefore improve stabilization of the implant 22 relative to the bone.

The talons 36 may be deployed between the first position X and the second position X' using an external driver (not shown) that is affixed to the implant 22 post insertion. In an embodiment, the external driver may engage an end of the intramedullary portion 28 of the implant 22 that is opposite from the talons 36 in order to be affixed to the implant 22. Turning the external driver in a first direction (e.g., clockwise) may deploy the talons 36 in a controlled manner. An audible clicking noise may be emitted to signify that the talons 36 have fully deployed to the second position X'. During removal, the external driver may be affixed to the implant 22 and then rotated in a second direction (e.g., counterclockwise) to retract the talons 36 back to the first position X. the implant 22 may then be safely removed without damaging the surrounding bone.

The implant 22, including the plate portion 26 and the intramedullary portion 28, may be made from any biocompatible material or combinations of biocompatible materials. Exemplary materials include, but are not limited to, titanium, titanium alloys, stainless steel, and thermoplastic materials.

With primary reference to FIG. 2, an exemplary surgical method to repair the bone abnormality 18 using the intramedullary implant system 20 may include the following non-limiting steps. After first exposing the first metatarsal 16-1, an osteotomy may be performed to divide the first metatarsal 16-1 into a distal segment 38 and a proximal segment 40. The distal segment 38 is then shifted in a direction toward the second metatarsal 16-2. Next, a intramedullary passage 42 may be drilled into the proximal segment 40 of the first metatarsal 16-1. The intramedullary portion 28 of the implant 22 may then be inserted into the intramedullary passage 42.

The plate portion 26 is then positioned against an external surface of the distal segment 38, and the fixation devices 24 may then be inserted through the openings 34 of the implant 22 and into the distal segment 38, the proximal segment 40, or both. In an embodiment, the third fixation device 24C extends at a transverse angle relative to the longitudinal centerline axis A of the intramedullary portion 28. Finally, the talons 36 of the intramedullary portion 28 may be deployed in order to enhance fixation and stabilization of the implant 22 relative to the first metatarsal 16-1.

Figure 4:
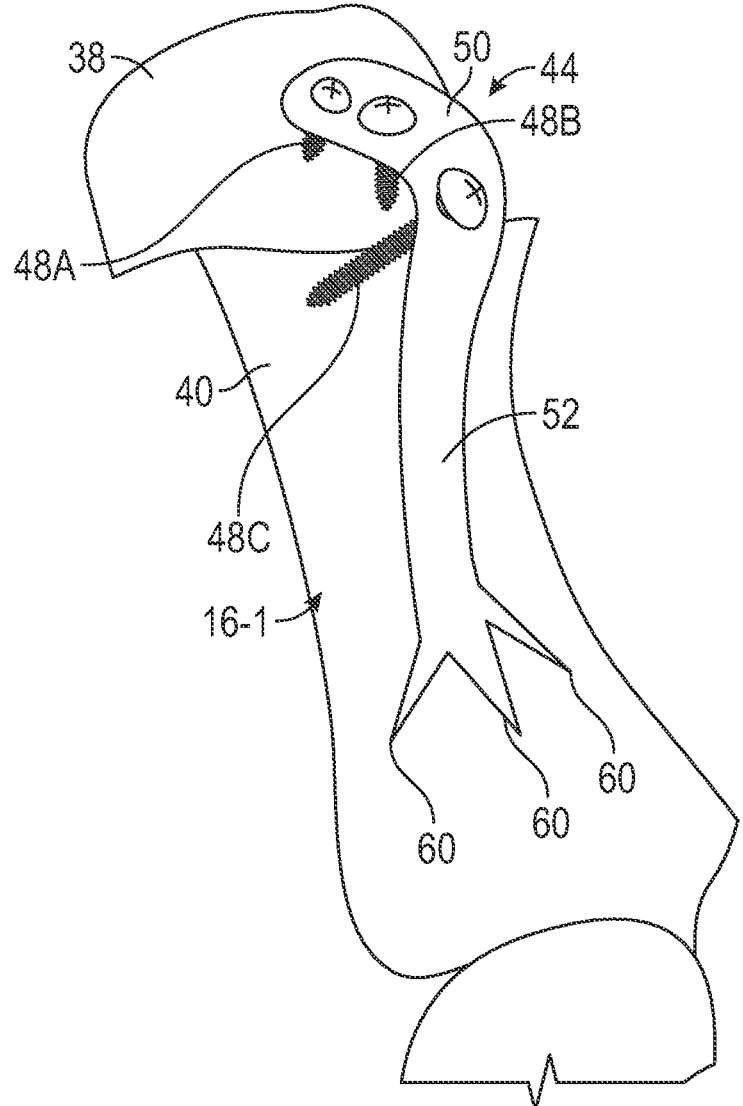
FIG. 4 illustrates another exemplary intramedullary implant system for correcting a bone abnormality.
Figure 5:
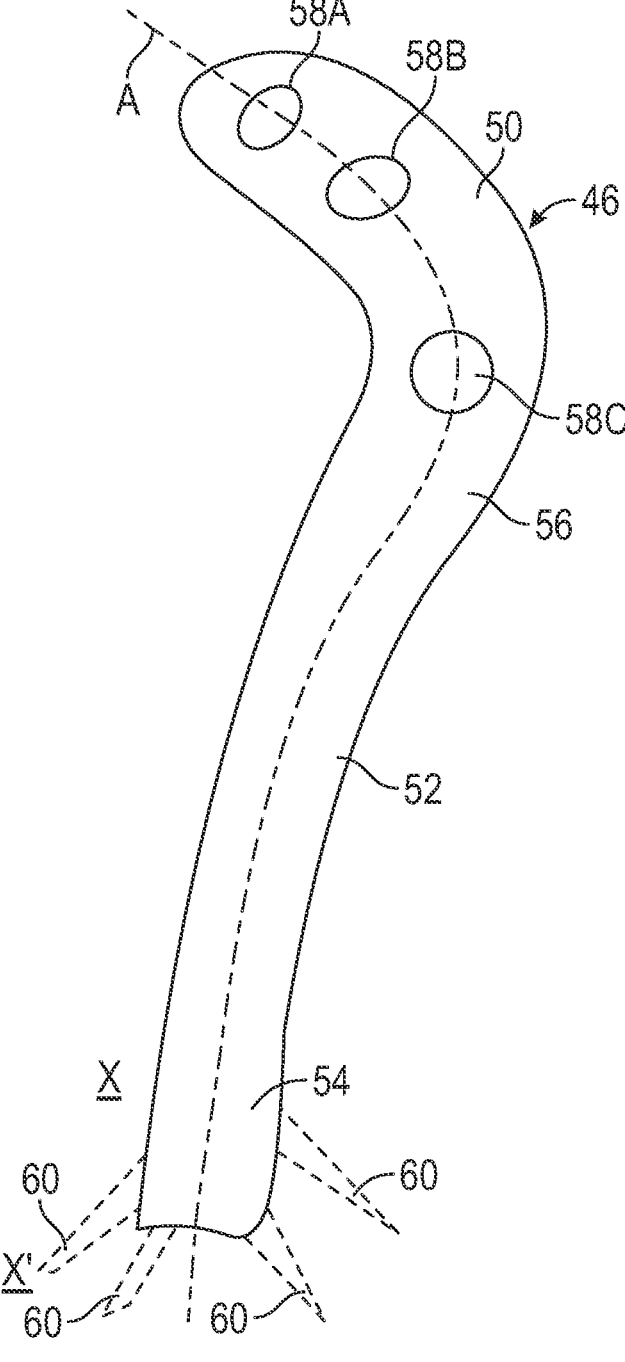
FIG. 5 further illustrates the intramedullary implant system of FIG. 4.

FIGS. 4-5 illustrate another exemplary intramedullary implant system 44 for repairing a bone abnormality, such as the bone abnormality 18 of FIG. 1. The intramedullary implant system 44 may include an implant 46 and a multitude of fixation devices 48 (e.g., screws, pegs, etc.).

The implant 46 may include a plate portion 50 and an integral intramedullary portion 52. In an embodiment, the plate portion 50 and the intramedullary portion 52 are integrated together as a single-piece structure. The implant 46 may be a monolithic device without any mechanical attachments for connecting the plate portion 50 and the intramedullary portion 52 together.

The implant 46 may extend along a centerline axis A. In an embodiment, the centerline axis A is non-linear, and thus, portions of the plate portion 50, the intramedullary portion 52, or both may be curved. The curvature of the implant 46 simplifies the ability to effect the metatarsal shift between the distal segment 38 and the proximal segment 40 of the first metatarsal 16-1 in order to repair the bone abnormality.

The intramedullary portion 52 of the implant 46 may extend between a proximal portion 54 and a distal portion 56. The distal portion 56 connects to the plate portion 50 of the implant 46, whereas the proximal portion 54 is disposed at an opposite end of the intramedullary portion 52 from the plate portion 50. Once implanted, the plate portion 50 is received against an external surface of the bone and therefore is an "extramedullary" component of the implant 46.

The plate portion 50, the intramedullary portion 52, or both may include openings for receiving the fixation devices 48. In an embodiment, the plate portion includes a first opening 58A for receiving a first fixation device 48A, a second opening 58B for receiving a second fixation device 48B, and a third opening 58C for receiving a third fixation device 48C. The first and second fixation devices 48A and 48B may be locking screws and the third fixation device 48C may be a crossing screw, in an embodiment.

In another embodiment, the intramedullary portion 52 of the implant 46 includes one or more deployable talons 60. The talons 60 may be selectively deployed between a first position X and a second positon X' (shown in phantom in FIG. 5). In the deployed positon X', the talons 60 grip surrounding bone and therefore improve stabilization of the implant 46 relative to the bone.

Figure 7:
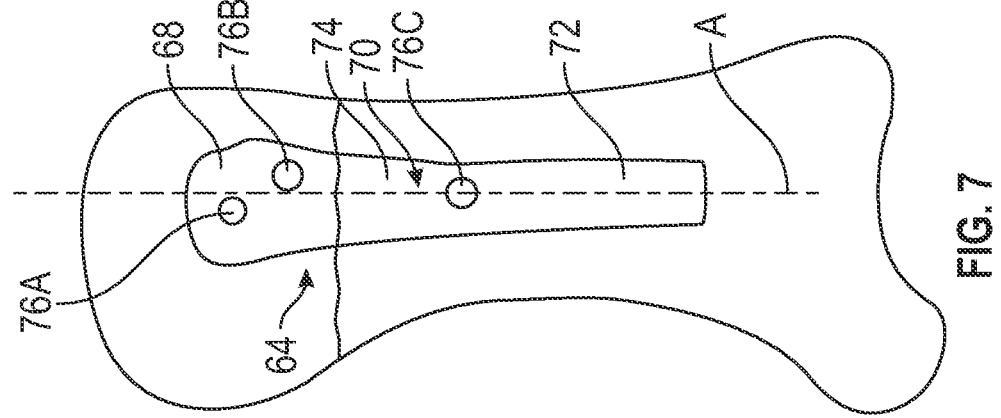
FIG. 7 further illustrates the intramedullary implant system of FIG. 6.
Figure 6:
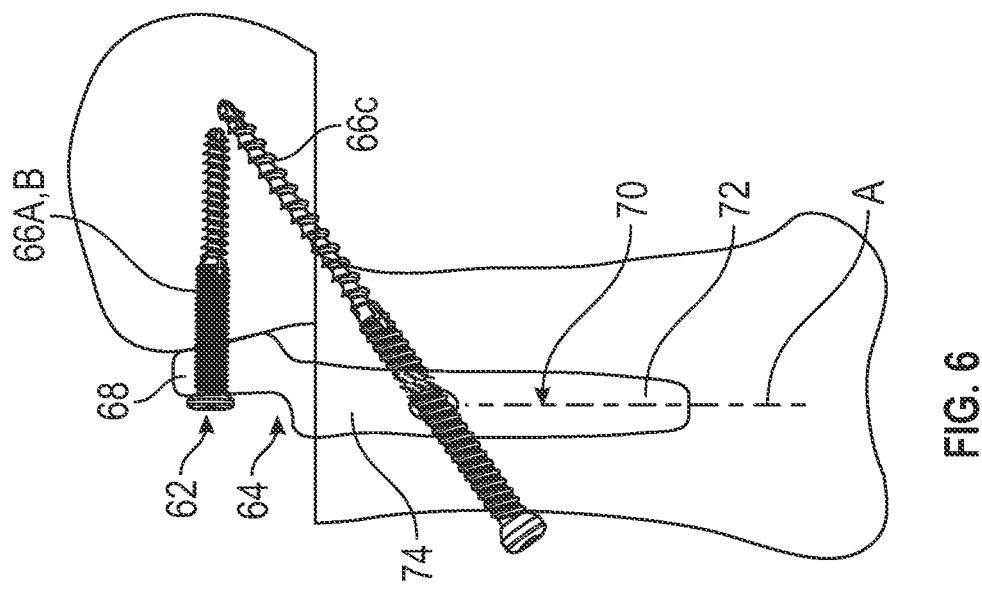
FIG. 6 illustrates yet another intramedullary implant system for correcting a bone abnormality.

FIGS. 6-7 illustrate another exemplary intramedullary implant system 62 for repairing a bone abnormality. The intramedullary implant system 62 is similar to the intramedullary implant system 20 of FIGS. 2-3 and includes an implant 64 and fixation devices 66. However, in this embodiment, the implant 64 of the intramedullary implant system 62 lacks talons.

The implant 64 may include a plate portion 68 and an integral intramedullary portion 70. The intramedullary portion 70, which may be configured in the shape of a nail body, may extend along a longitudinal centerline axis A between a proximal portion 72 and a distal portion 74. The plate portion 68 may include any size and shape. The distal portion 74 connects to the plate portion 68 of the implant 64, whereas the proximal portion 72 is disposed at an opposite end of the intramedullary portion 70 from the plate portion 68. Once implanted, the plate portion 68 is received against an external surface of the bone and is therefore an "extramedullary" component of the implant 64.

In an embodiment, the plate portion 68 is offset from intramedullary portion 70. For example, the plate portion 68 may be laterally offset from the longitudinal centerline axis A of the intramedullary portion 70. The offset between the plate portion 68 and the intramedullary portion 70 can be any offset distance within the scope of this disclosure (e.g., 3 mm, 5 mm, 7 mm, 10 mm, etc.).

In an embodiment, the plate portion 68 includes a first opening 76A for receiving a first fixation device 66A and a second opening 76B for receiving a second fixation device 66B, and the intramedullary portion 70 includes a third opening 76C for receiving a third fixation device 66C. The first and second fixation devices 66A and 66B may be locking screws and the third fixation device 66C may be a crossing screw, in an embodiment. The total numbers of openings and fixation devices of the intramedullary implant system 62 are not intended to limit this disclosure.

Figure 8:
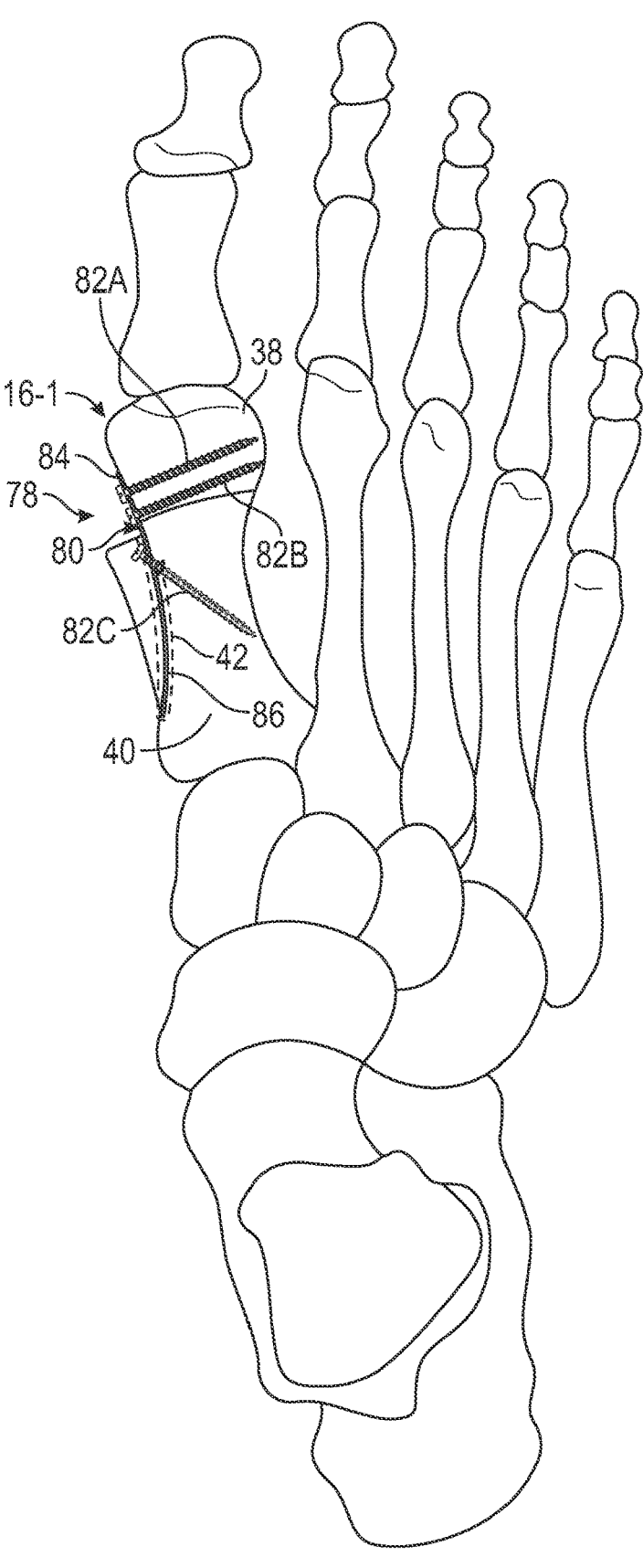
FIG. 8 illustrates yet another intramedullary implant system for correcting a bone abnormality.
Figure 9A:
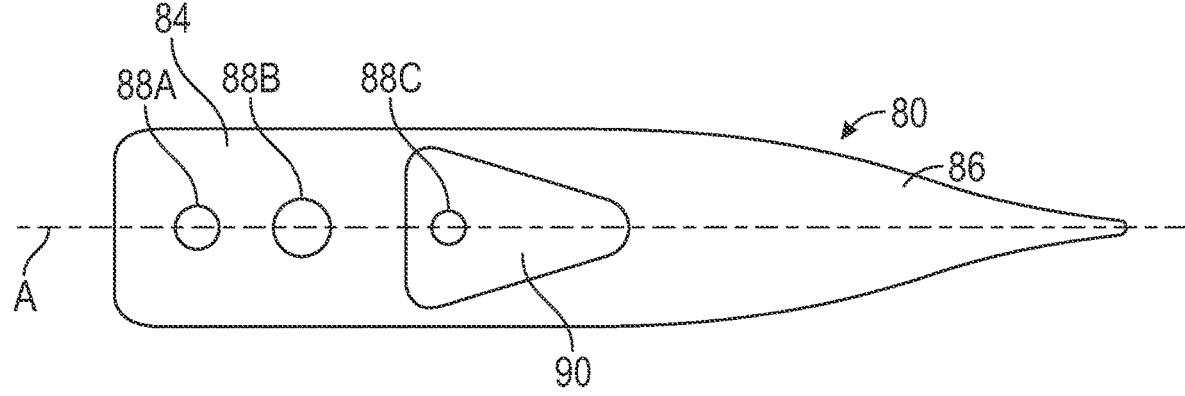
FIGS. 9A and 9B further illustrate the intramedullary implant system of FIG. 8.
Figure 9B:
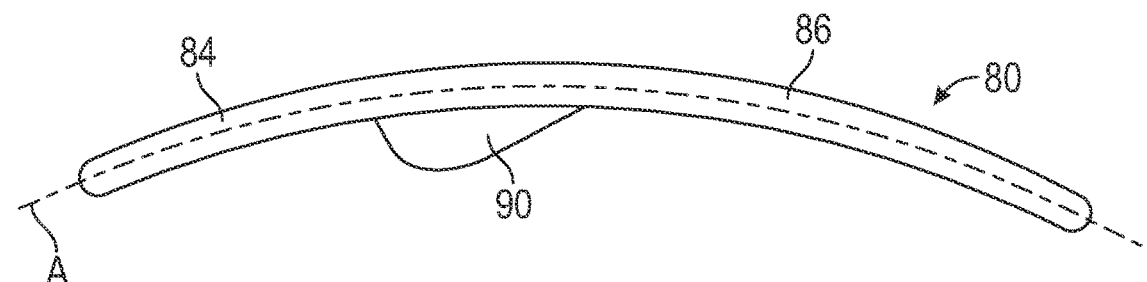

FIGS. 8, 9A, and 9B illustrate yet another exemplary intramedullary implant system 78 for repairing a bone abnormality. The intramedullary implant system 78 may include an implant 80 and a multitude of fixation devices 82 (e.g., screws, pegs, etc.) for fixating the implant 80 relative to bone, such as the first metatarsal 16-1.

The implant 80 of the intramedullary implant system 78 may be made from a shape memory material (e.g., material or materials capable of exhibiting superelasticity and/or a temperature-induced shape changes). In a first embodiment, the implant 80 is made of a metal alloy, such as Nitinol (NiTi). In another embodiment, the implant 80 is made of a polymer, such as an appropriately processed polyether ether ketone (PEEK). By virtue of its material make-up, the implant 80 can generate a compressive load in order to realign bones or bone segments at desired positions relative to one another and can maintain the compressive load while healing occurs.

The implant 80 may include a plate portion 84 and an integral intramedullary portion 86. Once implanted, the plate portion 84 is received against an external surface of a bone, such as a distal segment 38 of the first metatarsal 16-1, and is therefore an "extramedullary" component of the implant 80, and the intramedullary portion 86 may be inserted within an intramedullary passage 42 of a bone, such as a proximal segment 40 of the first metatarsal 16-1.

The implant 80 may extend along a centerline axis A. In an embodiment, the centerline axis A is curved. In combination with the shape memory material, the curvature of the implant 80 simplifies the ability to effect the metatarsal shift between the distal segment 38 and the proximal segment 40 of the first metatarsal 16-1 when repairing the bone abnormality.

The plate portion 84 may include a first opening 88A for receiving a first fixation device 82A and a second opening 88B for receiving a second fixation device 82B. The first and second fixation devices 82A and 82B may be locking screws, in an embodiment.

The intramedullary portion 86 may include a third opening 88C for receiving a third fixation device 82C. The third fixation device 82C may be a crossing screw, in an embodiment. The total numbers of openings and fixation devices of the intramedullary implant system 78 are not intended to limit this disclosure.

In another embodiment, the intramedullary portion 86 of the implant 80 includes a tab 90 that protrudes from the intramedullary portion 86 near a junction between the intramedullary portion 86 and the plate portion 84. The tab 90 may function to fill portions of an intramedullary passage 42 formed in the proximal segment 40 for accommodating the intramedullary portion 86. The third opening 88C may extend through the tab 90. Therefore, once inserted, the third fixation device 82C may be fixated through the tab 90.

Figure 10:
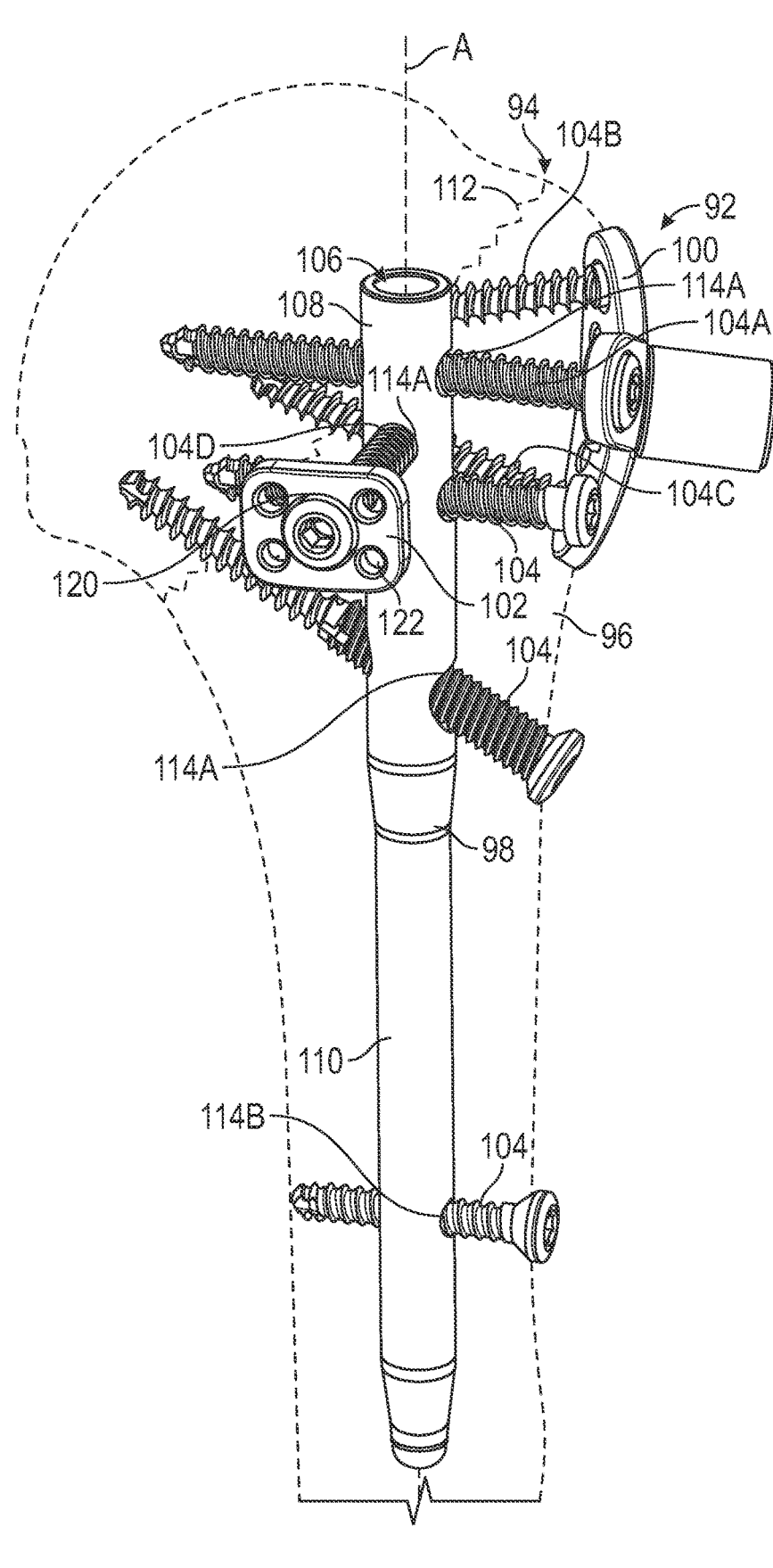
FIG. 10 illustrates an intramedullary implant system for repairing another bone abnormality.
Figure 11:
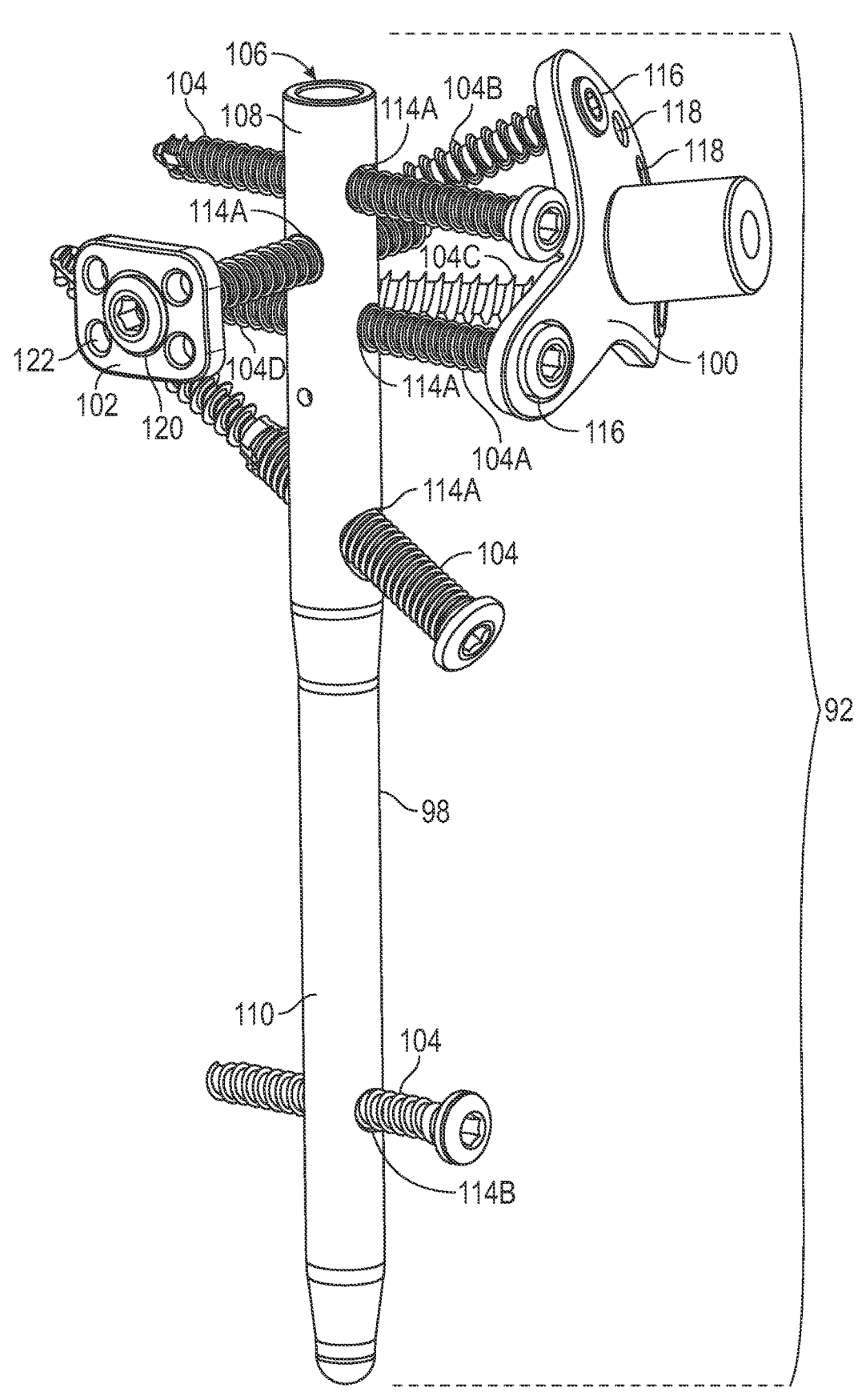
FIG. 11 further illustrates the intramedullary implant system of FIG. 10.

FIGS. 10-11 illustrate an exemplary intramedullary implant system 92 for repairing another bone abnormality 94 of a bone 96. In this embodiment, the bone abnormality 94 includes a fracture. The bone 96 may be a humerus or any other long bone. Although shown proximally, the fracture could be located anywhere on the bone 96.

The intramedullary implant system 92 may include an intramedullary nail 98, one or more plates 100, one or more washers 102, and a plurality of fixation devices 104. The total numbers of plates 100, washers 102, and fixation devices 104 used within the intramedullary implant system 92 are not intended to limit this disclosure.

The intramedullary nail 98 may include a cannulated body 106 that extends along a longitudinal centerline axis A between a proximal portion 108 and a distal portion 110. The proximal portion 108 may include a first plurality of openings 114A (e.g., holes or slots) for accommodating the fixation devices 104, and the distal portion 110 may include a second plurality of openings 114B for accommodating the fixation devices 104. In general, one fixation device 104 may be received through each opening 114A, 114B. However, it is not necessary for each opening 114A, 114B to be utilized during a given surgical procedure.

Figure 12:
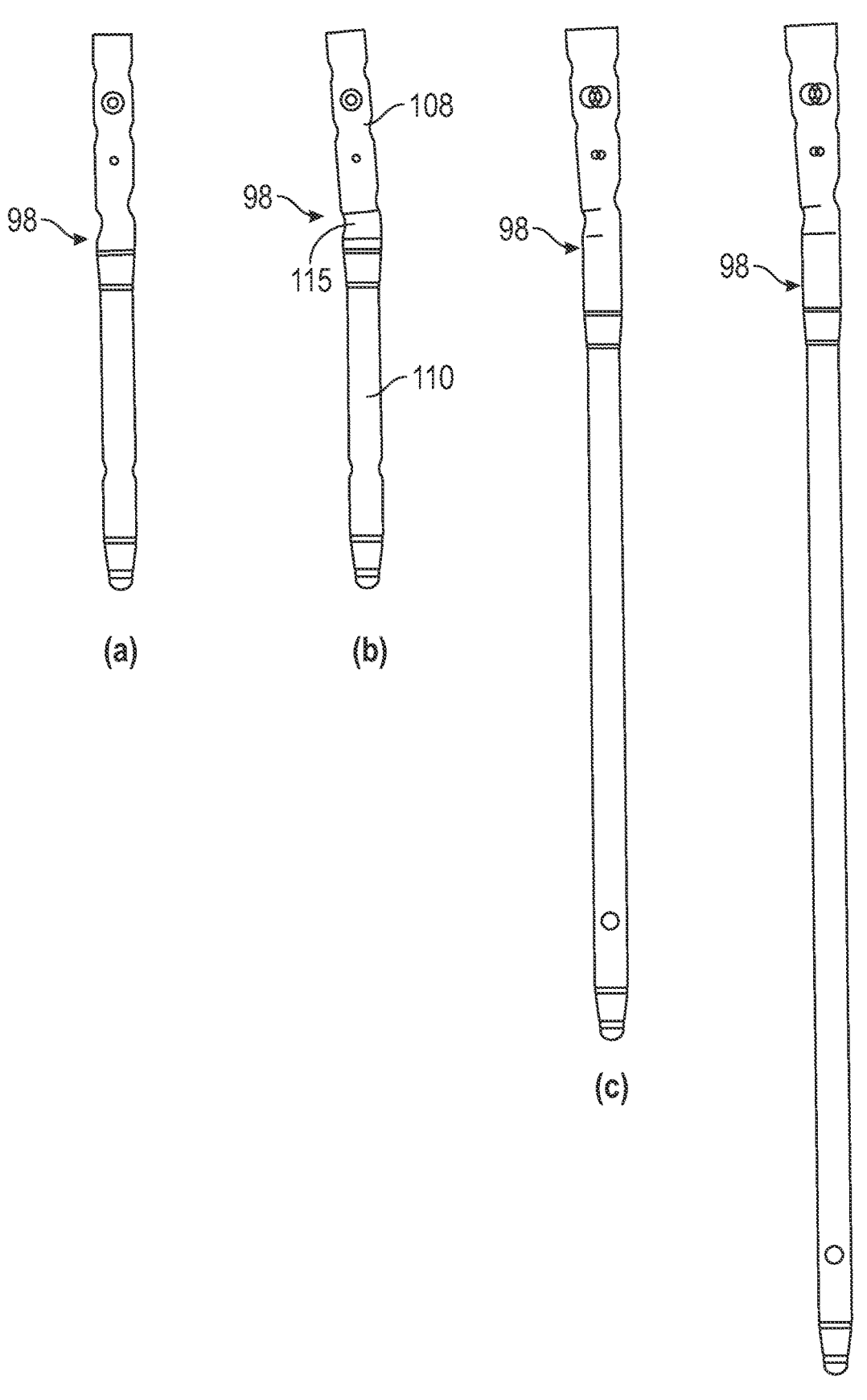
FIG. 12 illustrates various designs of an intramedullary nail of the intramedullary implant system of FIGS. 10-11.

The intramedullary nail 98 may embody various configurations. In an embodiment, the cannulated body 106 of the intramedullary nail 98 is completely straight along the longitudinal axis (see picture (a) of FIG. 12). In another embodiment, the proximal portion 108 of the cannulated body 106 is angled relative to the distal portion 110 to establish a slight bend 115 in the intramedullary nail 98 (see picture (b) of FIG. 12). In addition, depending on the size of the bone 96, the intramedullary nail 98 could include a small size (see pictures (a) and (b) of FIG. 12), a medium size (see picture (c) of FIG. 12), or a large size (see picture (d) of FIG. 12).

Once implanted in the bone 96, at least a portion of the intramedullary nail 98 may extend across a facture line 112 of the fracture. In the illustrated embodiment, a portion of the proximal portion 108 extends across the fracture line 112. However, this will ultimately depend on the location of the fracture and the type of bone, among other factors.

Figures 13A, 13B:
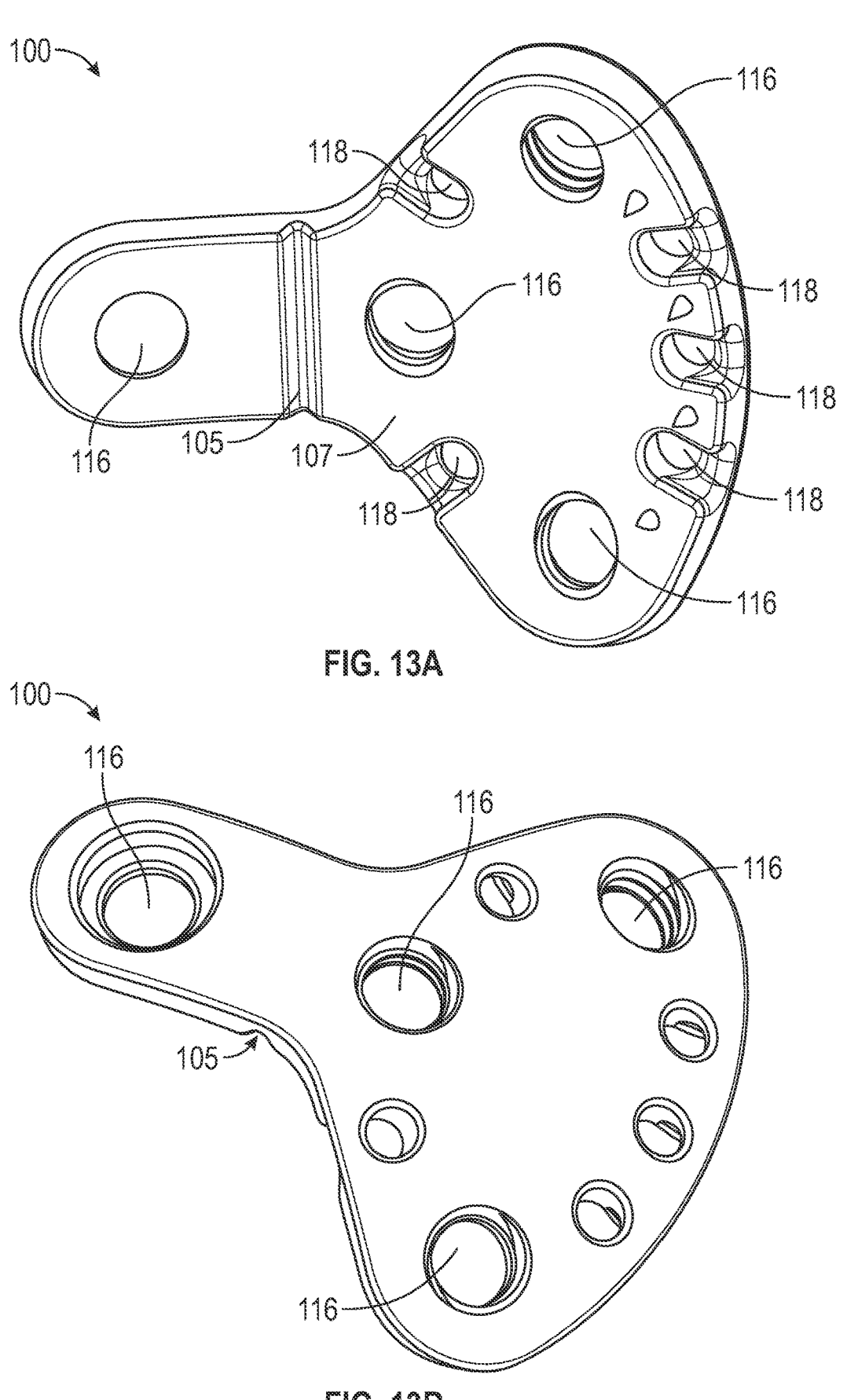
FIGS. 13A and 13B illustrate an exemplary plate of the intramedullary implant system of FIGS. 10-11.

One or more of the plates 100 may be utilized in conjunction with the intramedullary nail 98 in order to augment the fracture fixation. The plate 100 may include any size or shape (an exemplary plate 100 design is shown in FIGS. 13A and 13B).

The plate 100 may optionally include a groove 105 for allowing the bending/molding of the plate 100 to sit flush on differing bone anatomies or in differing bone locations. In an embodiment, the groove 105 is located on a bone facing surface 107 of the plate 100.

The plate 100 may additionally include a plurality of openings 116 that are configured to receive one of the fixation devices 104. In an embodiment, a fixation device 104A may be received within one of the openings 116 of the plate 100 and within one of the openings 114A, 114B of the intramedullary nail 98. The fixation devices 104A thereby locks the intramedullary nail 98 and the plate 100 together. Once locked together, the plate 100 can be rotated as desired to better approximate a fractured segment of the bone 96 back to its anatomical location. Additional fixation devices 104B and 104C may then be inserted through openings 116 of the plate 100 and into the bone 96 to repair the fracture.

The plate 100 may additionally include one or more suture holes 118. The suture holes 118 are configured to receive a suture, filament, or some other threadlike material for assisting in repairing the fracture and/or for tying tissue to the bone 96.

Figure 14A:
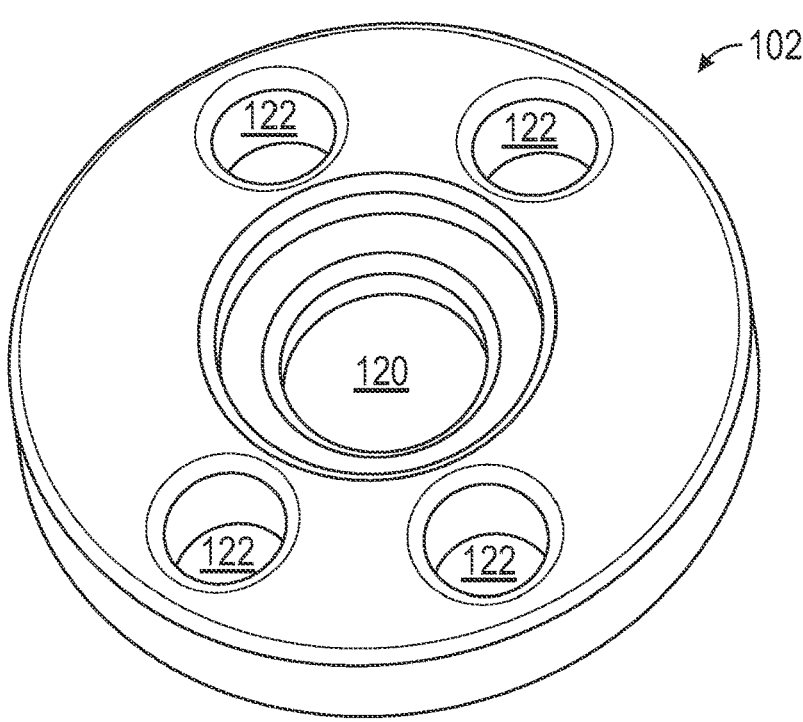
FIGS. 14A and 14B illustrate an exemplary washer of the intramedullary implant system of FIGS. 10-11.
Figure 14B:
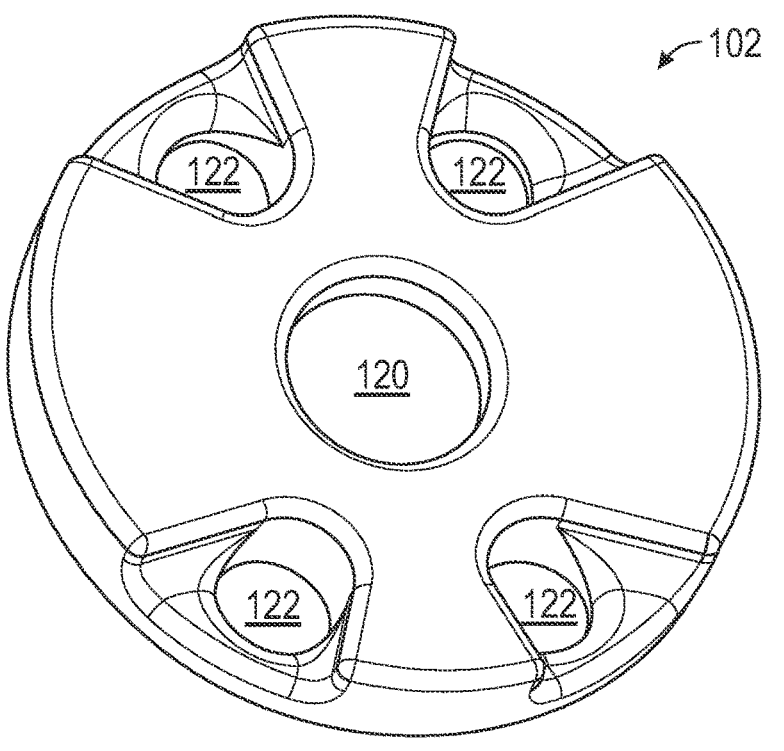
Figure 15A:
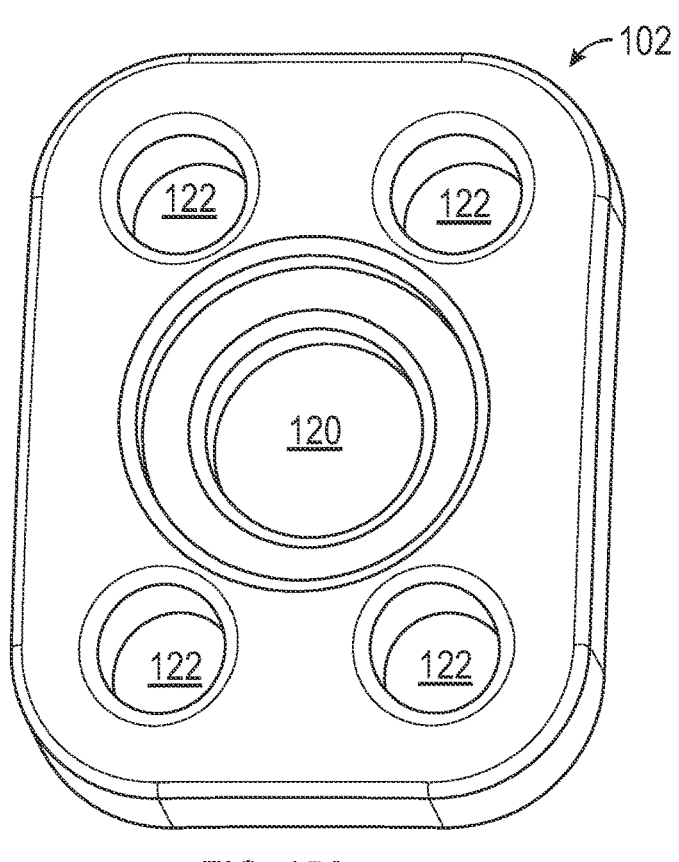
FIGS. 15A and 15B illustrate another exemplary washer of the intramedullary implant system of FIGS. 10-11.
Figure 15B:
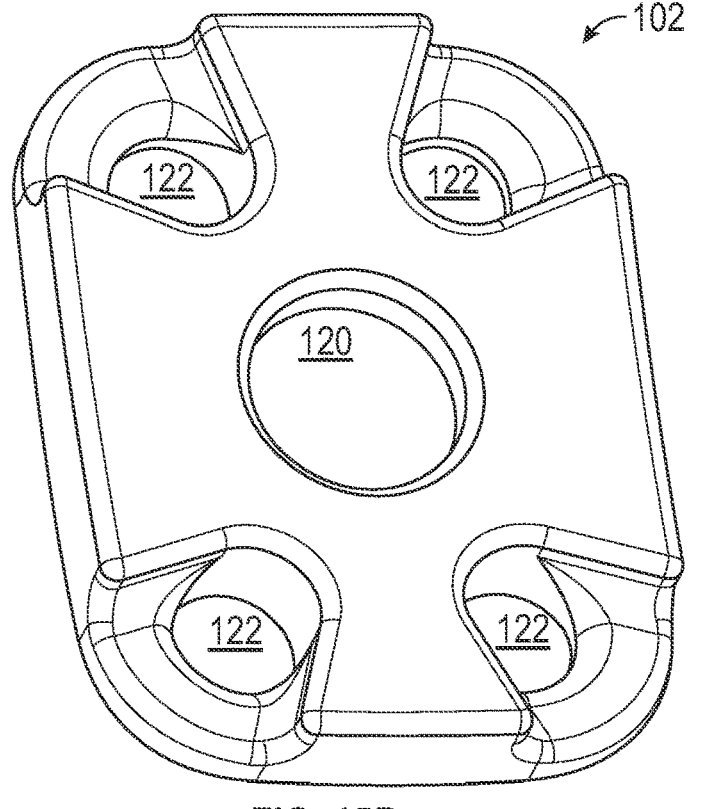

One or more of the washers 102 may additionally be utilized in conjunction with the intramedullary nail 98 in order to further augment the fracture repair. The washer 102 may include any size or shape. In a first embodiment, the washer 102 is round (see FIGS. 14A and 14B). In a second embodiment, the washer 102 is rectangular (see FIGS. 15A and 15B). Other shapes are also contemplated within the scope of this disclosure.

The washer 102 may include a central opening 120 that is configured to receive one of the fixation devices 104. In an embodiment, a fixation device 104D may be received within the central opening 120 and within one of the openings 114A, 114B of the intramedullary nail 98. The fixation devices 104D thereby locks the intramedullary nail 98 and the washer 102 together for augmenting the fracture repair.

The washer 102 may additionally include one or more suture holes 122. In an embodiment, the suture holes 122 surround the central opening 120. The suture holes 122 are configured to receive a suture, filament, or some other threadlike material for assisting in repairing the fracture and/or for tying tissue to the bone 96.

An exemplary method for using the intramedullary implant system 92 to repair a fractured bone may include the following exemplary method steps. The intramedullary implant system 92 can be implanted using percutaneous or open reduction techniques. First, fragments of the fractured bone can be pinned together for initial fixation. The intramedullary nail 98 may then be inserted into the bone using a radiolucent attachment which also functions as a guide for insertion of the fixation devices 104 and the plates 100 and washers 102. Fluoroscopy can be utilized to aid in final reduction of fracture fragments and assurance that the fixation devices 104 and plates 100/washers 102 are correctly placed to completely reduce the fracture fragments.

The intramedullary implant systems of this disclosure are configured for treating various bone abnormalities. Non-limiting examples of bone abnormalities that may be treated include hallux valgus procedures, bunionectomies, fracture repairs, fusion (i.e., arthrodesis) repairs, etc.

Moreover, the systems described herein have referenced surgery in humans. However, the implants of this disclosure can also be used in arthroplasty surgery in other animals, including but not limited to, dogs, horses, cats, cattle, etc.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. An intramedullary implant system, comprising:
   an implant including a plate portion and an integral intramedullary portion;
   a plurality of talons provided on the integral intramedullary portion and configured to deploy from a first position to a second position to increase a rotational stability of the implant relative to a bone;
   a locking screw received through an opening of the plate portion; and a crossing screw received through an additional opening of the plate portion or the integral intramedullary portion, wherein the crossing screw extends at a non-perpendicular angle relative to a centerline axis of the implant, wherein the plate portion is laterally offset from a longitudinal centerline axis of the integral intramedullary portion such that a majority of the plate portion is shifted laterally beyond both a first lateral side edge and a second lateral side edge of the integral intramedullary portion.

2. The intramedullary implant system as recited in claim 1, wherein the plurality of talons are provided on a proximal portion of the integral intramedullary portion.

3. The intramedullary implant system as recited in claim 2, wherein the plurality of talons includes a first row of talons and a second row of talons, wherein the second row of talons is distal to the first row of talons along the proximal portion of the integral intramedullary portion.

4. The intramedullary implant system as recited in claim 1, wherein the plurality of talons include deployable wings, barbs, claws, or any combinations thereof.

5. The intramedullary implant system as recited in claim 1, wherein the integral intramedullary portion is configured in a shape of a nail body, and the additional opening is formed through the nail body for receiving the crossing screw.

6. The intramedullary implant system as recited in claim 5, wherein the nail body is cylindrically shaped and includes a blunt end.

7. The intramedullary implant system as recited in claim 1, wherein the plate portion and the integral intramedullary portion establish a single-piece structure of the implant, and the single-piece structure excludes any mechanical attachments for connecting the plate portion and the integral intramedullary portion together.

8. The intramedullary implant system as recited in claim 1, wherein at least a portion of the plate portion is curved.

9. The intramedullary implant system as recited in claim 1, wherein at least a portion of the integral intramedullary portion is curved.

10. The intramedullary implant system as recited in claim 1, wherein at least a portion of both the plate portion and the integral intramedullary portion is curved.

11. The intramedullary implant system as recited in claim 1, wherein the plate portion establishes an extramedullary component of the implant.

12. The intramedullary implant system as recited in claim 1, wherein the crossing screw is received through the additional opening of the plate portion, and comprising a second locking screw received through a second additional opening of the plate portion.

13. The intramedullary implant system as recited in claim 1, wherein the locking screw extends through the opening along a first longitudinal axis, and the crossing screw extends through the additional opening along a second longitudinal axis.

14. The intramedullary implant system as recited in claim 13, wherein the second longitudinal axis diverges away from the first longitudinal axis in a direction of insertion of the crossing screw.

15. The intramedullary implant system as recited in claim 14, wherein the crossing screw is located proximally of the locking screw.

16. An intramedullary implant system, comprising:

an implant including a plate portion and an integral intramedullary portion;

a plurality of retractable talons provided on the integral intramedullary portion and configured to deploy from a first position to a second position to increase a rotational stability of the implant relative to a bone;

a first locking screw received through a first opening of the plate portion;

a second locking screw received through a second opening of the plate portion; and a crossing screw received through a third opening of the integral intramedullary portion, wherein the crossing screw extends at a non-perpendicular angle relative to a centerline axis of the implant, wherein the plate portion is laterally offset from a longitudinal centerline axis of the integral intramedullary portion such that a majority of the plate portion is shifted laterally beyond both a first lateral side edge and a second lateral side edge of the integral intramedullary portion, wherein the integral intramedullary portion is configured in a shape of a nail body, and the third opening extends through the nail body for receiving the crossing screw.

17. An intramedullary implant system, comprising:

an implant including a plate portion adapted for extramedullary fixation relative to a metatarsal bone and an integral intramedullary portion adapted for insertion into an intramedullary passage inside the metatarsal bone;

a first row of retractable talons provided on the integral intramedullary portion and configured to deploy from a first position to a second position to increase a rotational stability of the implant, a second row of retractable talons provided on the integral intramedullary portion and configured to deploy from a first position to a second position to increase the rotational stability of the implant, wherein the second row of talons is located distal to the first row of talons along a length of the integral intramedullary portion;

a first locking screw received through a first opening of the plate portion;

a second locking screw received through a second opening of the plate portion; and a crossing screw received through a third opening of the integral intramedullary portion, wherein the crossing screw extends at a non-perpendicular angle relative to a longitudinal centerline axis of the integral intramedullary portion, wherein the plate portion is laterally offset from the longitudinal centerline axis of the integral intramedullary portion such that a majority of the plate portion is shifted laterally beyond both a first lateral side edge and a second lateral side edge of the integral intramedullary portion, wherein the integral intramedullary portion is configured in a shape of a nail body, and the third opening extends through the nail body for receiving the crossing screw.

18. The intramedullary implant system as recited in claim 17, wherein the first row of retractable talons and the second row of retractable talons emit an audible clicking noise when deployed from the first position to the second position.

19. The intramedullary implant system as recited in claim 17, wherein the plate portion is connected to a distal portion of the integral intramedullary portion, and the first row of retractable talons and the second row of retractable talons are provided on a proximal portion of the integral intramedullary portion.

20. The intramedullary implant system as recited in claim 19, comprising an external driver engageable to a distal end of the distal portion and being rotatable for deploying the first row of retractable talons and the second row of retractable talons from the first position to the second position.

21. The intramedullary implant system as recited in claim 20, wherein the first row of retractable talons and the second row of retractable talons are simultaneously deployable in response to rotation of the external driver.

22. The intramedullary implant system as recited in claim 17, wherein the plate portion is laterally offset from the longitudinal centerline axis of the integral intramedullary portion by a distance between about 3 mm and about 10 mm.

23. The intramedullary implant system as recited in claim 22, wherein the offset is configured to accommodate anatomical variations of a metatarsal bone during hallux valgus correction.

\* \* \* \* \*